United States Patent [19]

Rhodes

[11] 4,358,358
[45] Nov. 9, 1982

[54] STATIC CONTINUOUS ELECTROPHORESIS DEVICE

[75] Inventor: Percy H. Rhodes, Huntsville, Ala.

[73] Assignee: The United States of America as represented by the Administrator of the National Aeronautics and Space Administration, Washington, D.C.

[21] Appl. No.: 309,293

[22] Filed: Oct. 6, 1981

[51] Int. Cl.³ .................. G01N 27/26; G01N 27/28
[52] U.S. Cl. ......................... 204/299 R; 204/180 R
[58] Field of Search ..................... 204/299 R, 180 R

[56] References Cited

U.S. PATENT DOCUMENTS

| | | | |
|---|---|---|---|
| 3,758,395 | 9/1973 | Strickler | 204/299 R |
| 3,847,773 | 11/1974 | Snyder | 204/299 R |
| 4,059,501 | 11/1977 | Strickler | 204/299 R |
| 4,309,268 | 1/1982 | Richman | 204/301 |
| 4,310,408 | 1/1982 | Rose et al. | 204/301 |

Primary Examiner—John F. Niebling
Attorney, Agent, or Firm—Joseph H. Beumer; John R. Manning; Leon D. Wofford, Jr.

[57] ABSTRACT

Apparatus is disclosed for carrying out a moving wall type electrophoresis process for separation of cellular particles. The Apparatus includes a water-tight housing (10) containing an electrolytic buffer solution. A separation chamber (12) in the housing is defined by spaced opposed moving walls (14 and 16) and spaced opposed side walls (18 and 20). Substrate assemblies (26 and 32), which support the moving wall include vacuum ports (60) for positively sealing the moving walls against the substrate walls. A plurality of suction conduits (62) communicate with the suction ports and are arranged in the form of valleys in a grid plate (64). Raised land portion of the grid plate support the substrate walls against deformation inwardly under suction. Cooling chamber (70) carried on the back side of plate (64). The apparatus also has tensioner means including roller (80) and adjustment screws (82) for maintaining the belts in position and a drive arrangement including an electric motor (90) with a gear (94) affixed to its output shaft. Electrode assemblies (56 and 57) are disposed to provide the required electric field.

15 Claims, 5 Drawing Figures

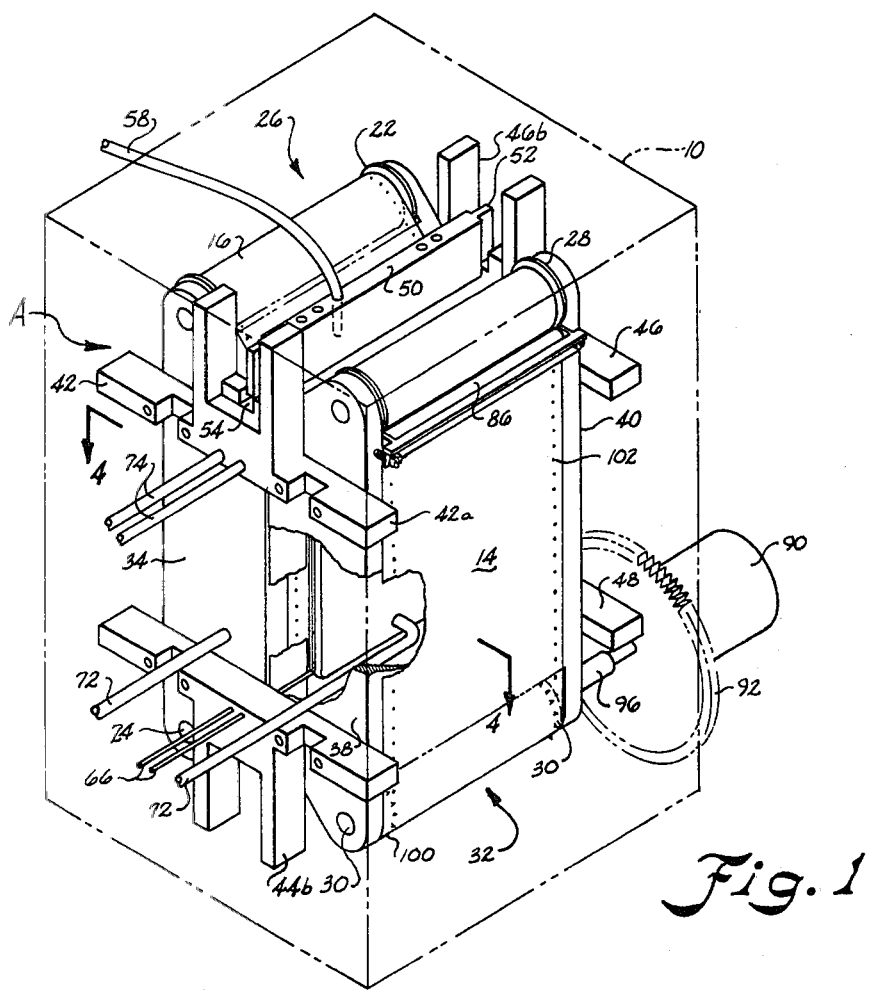
Fig. 1
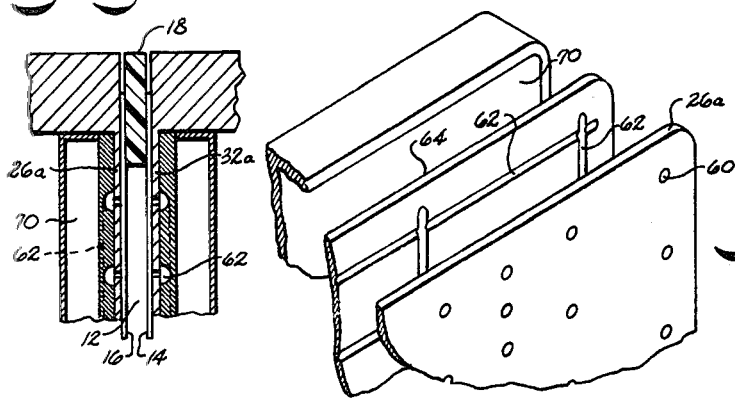
Fig. 4a
Fig. 2

STATIC CONTINUOUS ELECTROPHORESIS DEVICE

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

The invention relates to the electrophoresis process wherein biological cells, colloidal particles, or macromolecules with a net electrical charge migrate and separate in a solution under the influence of an electrical field and, more particularly, to improved apparatus for carrying out such a process.

Heretofore, conventional continuous electrophoretic separation devices have utilized a flat rectangular separation chamber to contain a flowing curtain of buffer in which a specimen is injected and where the separation process is conducted. An electrical field across the width of the chamber causes the injected sample cells to be separated into fraction bands through differential migration of the sample fractions. An array of collection receptacles located along the lower portion of the chamber collects the fractionated bands and hence provides for a continuous separation and collection of injected sample.

However, when fluid flows in a rectangular chamber, a parabolic velocity profile (Poiseuille flow) is established across the thickness of the chamber due to the no-slip boundary condition at the chamber walls. The Poiseuille flow of the buffer curtain causes sample particles distributed throughout the curtain thickness to have varying residence times in the chamber. This causes the deflection of a particle near the curtain midplane to be less than that for a similar particle near the chamber wall, providing distortion (crescent formation) of an initially straight injected sample band.

Adding to flow distortion is an effect known as electroosmosis which, as opposed to Poiseuille flow, causes a slip condition to occur at the chamber wall which produces an effect opposite to that of the Poiseuille distortion. Electroosmosis is a lateral flow across the width of the chamber which exists when charged walls are present.

As a result of laminar flow, a particle traveling through the separation chamber at or near the center plane will be deflected less than an electrophoretical similar particle moving through at some distance from the center plane. Therefore, an initially regular pattern of injected sample will be distorted into a convex shape when viewed in the direction of sample migration. On the other hand, electroosmotic flow increases the deflection of particles at on near the center plane so that concave patterns are formd when viewed in the direction of sample migration. These phenomena combine to produce crescent-shaped distortions which produce a variation in resolution across the chamber collection width. The curvature of the crescent-shaped distortions is determined by the flow that predominates--laminar flow or electroosmosis. Therefore, unless exact compensation exists, a bending of the injected sample band will result--an artifact which we will call flow distortion. The condition for exact compensation for these flow effects is the equality of sample and wall zeta potential. Maximum resolution occurs for an equality of charge (zeta potential) between the chamber walls and specific sample fraction. Since the wall usually has only one zeta potential, only one fraction can be in focus. A more thorough discussion of this phenomena may be found in Strickler, A. and Sacks, T. *Preparative Biochemistry*, 3, p. 269-277 (1973).

Due to the difficulty encountered in nullifying the above mentioned distortions, the sample stream is usually injected only in the center plane region of the chamber thickness. This practice is not only inefficient in the use of the chamber volume, but it is also a very unreliable method to control distortion because there are no positive means assuring maintenance of the sample near the chamber center plane. Therefore, during actual operation of a conventional continuous flow device, the sample deviates from the center plane region of buffer to marginal zones, establishing a limit on resolution.

An inherent disadvantage of any electrophoresis process is its inability to self-sharpen or self-stabilize the fraction bands during separation. The self-sharpening ability is called "focusing" and an example of which is isoelectric focusing. Not only does the focusing capacity lead to reliable long term processing durations, but it also increases throughput by allowing sample to be injected throughout the entire chamber volume.

Prior electrophoresis devices have been proposed for operation in space such as disclosed in Bier et al., "Preparative Electrophoresis in Zero Gravity," *Journal of Colloid and Interface Science*, 55, No. 1 (Apr. 1976) and Strickler, "Deflected-Laminar Electrophoresis," American Institute of Aeronautics and Astronautics Paper No. 77-233 (1977). However, these devices were intended only to improve throughout and not resolution. Most methods proposed to date for solving the flow distortion problem have merely sought to compensate for the disturbance rather than remove it. Operating in such a manner is rather like a balancing act and is not conducive to reliable operation. In addition, only one component of the sample will be in "focus" at any one time.

The thick chamber for use in zero gravity is a method which does not involve compensation. The increase in resolution would be achieved by keeping the sample away from the chamber walls via the increased chamber thickness and, hence, reduce sample band distortion. However, the resolution decreases with increasing chamber thickness for constant power dissipation in the chamber because the increase in thickness will also dictate a lower applied voltage for constant mid-plane temperature. Thus, merely increasing the chamber thickness without considering the impact on other operational parameters does not increase the resolution of separation.

Another method to eliminate flow disturbances was advanced in Kolin, A., Ellerbroek, B. L., "Theory of Simultaneous Multiple Streak Collimation in Continuous-Flow Electrophoresis by Superposition of Electro-Osmosis and Thermal Convection," *Separation and Purification Methods* 8, 1-19 (1979). This method, which might be thought of as the ultimate in compensation, uses a cross flow to neutralize electroosmosis and relies on thermal convection to blunt the parabolic flow-through profile sufficiently so that the center-plane region of the chamber will be distortion free. The power levels necessary to cause the required deformation of the parabolic flow-through profile are many times the power level limit that will disrupt electrophoresis in conventional separation chambers. Also, the exact and uniform counter flow along the length of the chamber necessary to counter electroosmosis would be very difficult to achieve. While this scheme is possible theoretically, it is practically impossible to implement successfully.

Probably the most practical idea yet employed to compensate for chamber flow distortions was developed in Strickler, A., Sacks, T., "Focussing in Continuous Flow Electrophoresis System by Electrical Control of Effective Cell Wall Zeta Potential." *Annals of New York Academy of Science* 209 (1973). The concept consisted of coating longitudinal sections of the inner chamber wall with materials having different zeta potentials and sectioning the respective electrodes so that the electrical field could be independently applied to each section. By controlling the electrical field strength in each section, flow distortions (crescent formations) created in a previous section could be compensated in a subsequent section simply by turning a control knob to change the applied voltage. The "focusing" process, however, had to be controlled by visual observation through a cross-section illuminator which revealed the crescent-shaped band cross sections. Although this concept is theoretically sound and workable, it has not found great acceptance in the field. It is impractical that the system requires a constant operator interface to maintain precise "focusing." Small changes in zeta potential matching can cause large changes in resolution.

It, therefore, appears that new methods and design concepts must be brought to overcome the problem of sample stream distortion, leading to a new device which would offer unique capabilities for operation, particularly in reduced gravity, and offer a significant improvement in resolution over similar ground-based machines. As proposed herein, these objectives are met by a concept and apparatus which utilize moving separation chamber walls. The moving walls entrain the fluid to flow as a rigid body, hence eliminating Poiseuille flow. All of the sample throughout the chamber thickness is thus exposed to the imposed electric field for the same period of time, while electroosmosis has been eliminated through the use of film-forming latexes. The zeta potential of the latex has been altered by prior coating of the particle surface with Methylcellulose which has been found to yield a zeta potential near zero. Since both sources for the disturbances have been eliminated, no compensation is required. The system operates like a static device while providing throughput like a conventional continuous-flow system. In addition, no limitation is placed on the usable fraction of the chamber thickness.

Accordingly, an important object of the present invention is to advance the state-of-the art in continuous electrophoresis devices and specifically to increase the resolution and throughput of such devices by the elimination of distortion problems associated therewith.

Another important object of the present invention is to provide a continuous electrophoresis device in which the buffer and specimen flow is generally static with respect to walls of the separation chamber.

Another important object of the present invention is to provide a static continuous electrophoresis device in which laminar flow distortion of the sample bands is virtually eliminated.

Yet another important object of the present invention is to provide a static continuous electrophoresis device in which electroosmosis is eliminated.

Yet another important object of the present invention is to provide a device which will optimize performance in such a manner as to make processing of biological cells feasible in space.

SUMMARY OF THE INVENTION

The above objectives are accomplished according to the present invention by providing an electrophoresis device having moving walls in which a static relationship is developed between the moving walls and the fluid and wherein the moving walls are provided by belts which are coated with a substance which prevents electroosmosis.

The static continuous electrophoresis device utilizes two coated MYLAR belts moving in synchronization which intrain the buffer to move as rigid body. The buffer does not flow as with conventional continuous electrophoresis devices but is static with respect to the moving walls. Since no flow takes place in the chamber, no parabolic velocity profile is present. With the electrodes parallel to the direction of motion of the belts, electrophoresis of an injected sample filament can be accomplished. Buffer and sample move through the chamber and separation of fractions is accomplished by a conventional array of collection ports along the lower width of the chamber. With the electrodes set at an angle to the direction of motion of the belts, electrophoretic focusing of an homogeneous mixture of sampling and buffer can be accomplished. In this configuration, one component of the belt motion opposes the electrical field while the other component carries the sample through the chamber. For a specific fraction, where the sample velocity component in the direction of the electrical field is equal to the electrophoretic migration velocity, a null point exists with respect to velocity perpendicular to the field. Therefore, the specific fraction remains at its null point while all other fractions migrate away to either side; hence, effecting a separation which we may call electrophoretic focusing.

The invention can be used to perform continuous isoelectric focusing as well as continuous isotachophoresis. The fact that the fluid is static allows for extremely low residence time which is imperative for any focusing technique.

The technique of static continuous electrophoresis apparatus eliminates sample band distortion by utilizing moving walls to obtain rigid body motion of the buffer; and by utilizing a low zeta-potential coating on the moving walls to control electroosmosis. The elimination of sample band distortion allows for the use of very "thin" chambers which are resistant to buoyance induced disturbances present in earth gravity. In reduced gravity, the chamber thickness may be increased to provide improved throughput. Since the entire chamber thickness can be used, this technique is much more efficient than standard chamber designs. In addition, the apparatus lends itself to numerous focusing techniques which are noted for their high stability of operation.

BRIEF DESCRIPTION OF THE DRAWINGS

The construction designed to carry out the invention will be hereinafter described, together with other features thereof.

The invention will be more readily understood from a reading of the following specification and by reference to the accompanying drawing(s) forming a part thereof, wherein an example of the invention is shown and wherein:

FIG. 1 is a perspective view illustrating static continuous electrophoresis apparatus constructed according to the invention;

FIG. 2 is a perspective view illustrating a substrate assembly front wall for supporting a moving separation chamber wall in a partially exploded view as constructed in accordance with the present invention;

FIG. 4a is an enlarged schematic illustration and partial cross-section view of a separation chamber side wall and sealing arrangement constructed according to the present invention.

DESCRIPTION OF A PREFERRED EMBODIMENT

Figure 3:
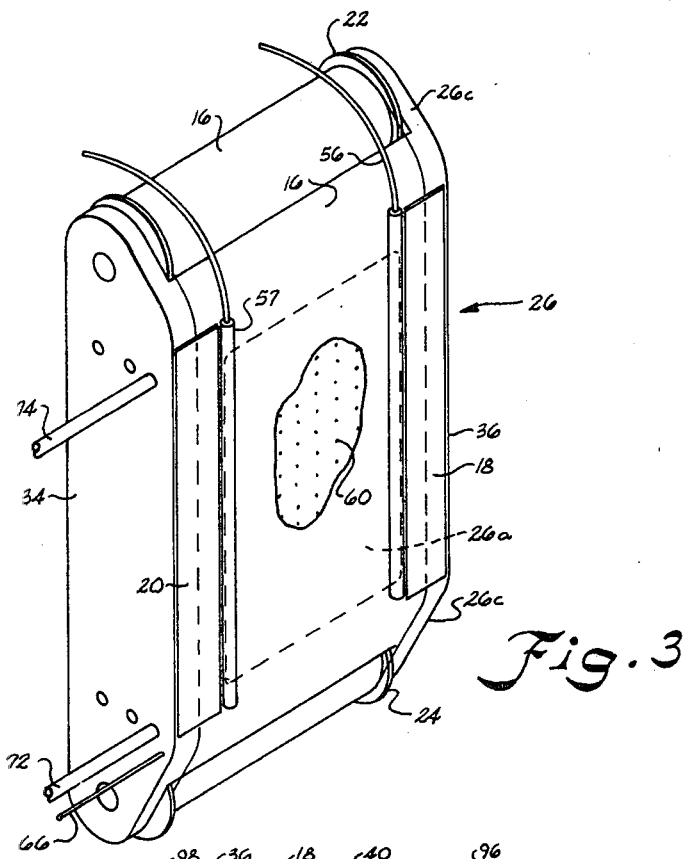
FIG. 3 is a perspective view of a substrate assembly and moving wall section of a static separation chamber constructed according to the present invention.

Referring to the drawings, apparatus is disclosed which includes a transparent water-tight enclosure housing 10 in which electrophoresis apparatus designated generally as A is enclosed in a suitable electrolytic buffer solution. The electrophoresis device includes a separation chamber 12 which is defined by moving belts 14 and 16 and stationary side walls 18 and 20. Belts 16 travel continuously about belt rollers 22 and 24 and about a substrate assembly designated generally as 26. Roller 22 is an idler roller and roller 24 is in the form of a drive roller which will be described more fully hereinafter. Endless belt 14 travels about rollers 28 and 30 about substrate assembly 32 wherein rollers designated generally as 28 and 30 are idler and drive rollers, respectively.

Belt rollers 22 and 24 are carried by integral side frames 34 and 36 of assembly 36 and belt rollers 28 and 30 by integral side frames 38 and 40 of assembly 32. Substrate assembly 26 further includes a front wall 26a and back wall 26b which bridge the side frames 34 and 36. Substrate assembly 32 includes front wall 32a and back wall 32b which bridge side frames 38 and 40.

Side frames 34 and 38 are affixed to brace supports 42 and 44 by any suitable means such as bolts. The brace supports 42 and 44 include horizontally and vertically extending legs 42a, 42b, 44a and 44b which engage the inner walls of the container 10 to support and properly position the electrophoresis apparatus within the container. Sidewalls 36 and 40 are affixed to brace supports 46 and 48 in a like manner which also comprise horizontal and vertical legs to support and position the apparatus.

Figure 4:
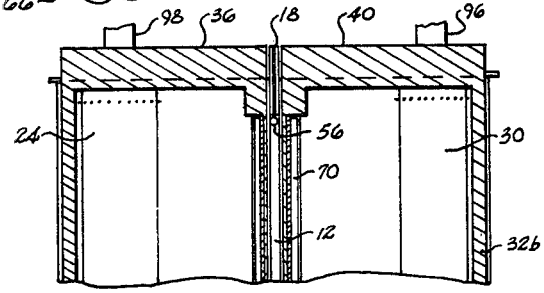
FIG. 4 is a cross-section of a separation chamber of static continuous electrophoresis apparatus according to the present invention.
Figure 4:
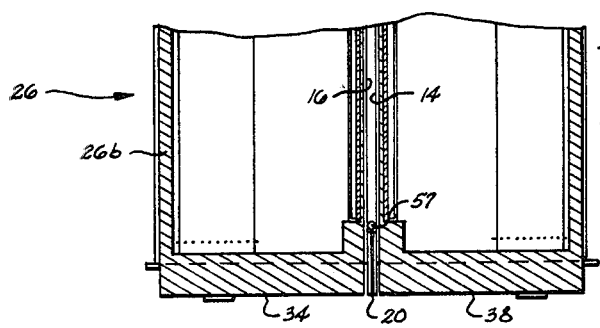

As best seen in FIG. 4a, side walls 18 and 20 provide means for sealing the edges of the belts 14 and 16 against the respective substrate front walls to prevent seepage behind the belts. For this purpose, side walls 18 and 20 may be formed from a rubber or rubber-like material. The sidewalls 18 and 20 may be fixed to either substrate front wall 26a or 32a and sandwiched therebetween overlying the film belts.

The MYLAR belts 14, 16 are coated with a low zeta-potential coating at 49 to control electroosmosis and for this purpose methylcellulose has been found particularly suitable as a coating.

A support panel 50 is carried above the separation chamber and includes reduced ends 52 which are inserted in slots 54 formed in upper brace supports 42 and 46. Support panel 50 holds electrode assemblies 56 and 57 as well as specimen insertion means 50 by receiving same in bores formed therein. A similar support panel (not shown) may be carried at the bottom of the separation chamber to support opposing ends of the electrodes. The electrode assemblies may be any conventional electrode assemblies.

A plurality of suction ports 60 are formed in and carried on the exterior faces of front substrate walls 26 and 32 which underlie the belts. The suction openings 60 communicate with a grid of suction conduits 62 formed in a plate 64 affixed to the back side of the substrate wall as best illustrated in FIG. 2. The raised lands of such grid plate structure reinforces and supports the front plate 26a, 32a against deformation and bowing in as would permit leakage as would be the possible case if a hollow vacuum chamber were employed behind the front plate.

A source suction line 66 is connected to a suction conduit 62 so as to provide a vacuum means which places a suction uniformly on the back side of traveling film belt 16 ensuring that the same adheres well to substrate wall 26 and that no leakage of fluid behind the film occurs as would cause flow distortions in the sample band.

Cooling means is provided by a cooling chamber 70 carried on the back side of the suction chamber or plate 64 to cool the fluid in the separation chamber. For this reason, substrate wall and suction chamber are made thin relative to the cooling chamber, like on the order of 3 to 1, to bring cooling fluid close to the chamber for effective cooling and reduction of Joule effect. The cooling chamber 70 is connected to a cooling inlet 72 and a cooling outlet 74 through which the coolant is circulated. The construction of suction and cooling chambers is identical for each substrate assembly.

Tensioner means 80 is provided for maintaining the belt tension of film belts 14 and 16 so that the traveling belts properly and tightly adhere to the walls of the respective substrate assemblies, particularly in the area of the separation chamber so that the belt is sealed against the front walls for more effective adherence by the vacuum means so as to prevent leakage of fluid. The tension means includes a roller 80 which may be adjusted in and out generally normal to the belt by means of adjustment screws 82 to vary the belt tension as required. Furthermore, the substrate wall 26a may be sloped at 26c in such a way that forces exerted on the belt as it travels tend to pull the belt against the substrate wall for sealing.

The belts are driven in an endless manner by means of a drive arrangement which includes an electric motor 90 having a gear 94 affixed to its output shaft (not shown). The gear is also affixed to the end of a shaft 96 which drives roller 30. A similar gear (not shown) is affixed to the shaft 98 of roller 24 and meshed with gear 94 so that the belt rollers 30 and 24 are driven in synchronism. The drive arrangement which includes the motor gears is disposed on the exterior of the housing 10 and, of course, all shaft and conduit lines through housing 10 are sealed.

In one exemplary construction, a separation chamber width of about 6 cm. and thickness of 1 mm. were utilized. Belts 14 and 16 were of a width of 9.75 cm. Side walls 18 and 20 were approximately 1 mm. in thickness and a width of 3 cm.

Belt rollers 24–30 include teeth 100 which engage in performations 102 formed in the marginal edges of belts 14 and 16 so that no belt slippage occurs as might induce flow disturbances. A slotted 20-gauge hypodermic needle (not shown) connected to insertion means 58 serves to inject the sample into the total thickness of the separation chamber 12.

Suction front walls 26a, 32a; the wall shape at 26c, 32c; belt tensioning means; and side walls sealing and construction provide means by which leakage of buffer past the side walls and behind the belts is prevented to avoid inducing specimen band distortion.

While the electrode assemblies 56, 57 have been shown inside the separation chamber 12, they may also be located outside the chamber so as to not take up space therein. In this case, the electrode assemblies may be carried in bores formed in brace supports 42, 44, 46, and 48 closely adjacent spacer side walls 18, 20. The side walls are then constructed to have a plastic stiffener 0.005 inches thick laminated between two pieces of blotter paper such as solvent wick paper available from Muttenz-Schweig of West Berlin, Germany. The blotter paper upon saturation with the buffer solution conducts the electrical flow from the adjacent electrode assemblies into the separation chamber.

Of course, it is to be understood that any conventional collection array and chamber may be employed at the bottom of the separation chamber 12 to collect the fractionated band or bands, and that such would be well within the skill of the average artisan. Also, this separation chamber may be operated in the horizontal phase i.e., with the gravity vector perpendicular to the direction of sample motion. This arrangement is particularly attractive from thermal connection considerations in that a stabilizing thermal gradient may be induced between the upper and lower chamber walls. Sample material settling to the bottom wall would still be carried through the chamber and separated. This horizontal operation could not be carried out in a static wall chamber.

While a preferred invention has been described using specific terms, such description is for illustration purposes only, and it is to be understood that changes and variations may be made without departing from the spirit or scope of the following claims.

What is claimed is:

1. Electrophoresis apparatus for separating colloidal and macromolecular cellular particles of the type having a separation chamber in which said particles are separated into at least one fraction band of a cellular species, sample insertion means for inserting a sample stream containing said particles into a buffer solution in said separation chamber and electrode assemblies creating an electrical field in said separation chamber whereby said cells separate into said fraction bands; said apparatus comprising:
   a water-tight enclosure housing containing said buffer solution;
   said separation chamber being carried within said enclosure housing;
   said separation chamber including a pair of spaced opposed moving walls and spaced opposed side walls defining said separation chamber;
   a pair of substrate assemblies having opposed front walls facing said separation chamber and one another;
   an endless traveling belt carried by each said substrate assembly defining said moving walls;
   vacuum means adhering each one of said belts to a respective front wall positively;
   means sealing marginal edges of each said traveling belt preventing leakage of said solution past said edges and said side walls; and
   drive means for moving said belt about said substrate assembly in an endless fashion without slippage.

2. The apparatus of claim 1 including cooling means carried by said substrate assembly adjacent said moving wall cooling said separation chamber.

3. The apparatus of claim 1 wherein said electrode assemblies are carried in said separation chamber parallel to said moving walls.

4. The apparatus of claim 1 wherein said vacuum means includes a plurality of suction ports formed in said front walls against which said belt is held by suction and a plurality of suction conduits interconnecting said suction ports in the form of grid means which supports said front plate against deformation inwardly.

5. The apparatus of claim 1 wherein each said substrate assembly includes:
   a pair of belt rollers about which said belt carried thereon travels;
   said belt rollers including teeth and said belts including marginal edge performations engaged by said teeth whereby said belts are driven endlessly without slippage.

6. The apparatus of claim 1 or 5 wherein each said front wall includes a slope portion exerting a force on said belt traveling thereover pulling said belt tightly against said wall for sealing.

7. The apparatus of claim 1 including tensioning means maintaining each said belt tensioned and tightly held against the walls of said substrate assemblies assisting in the prevention of said leakage.

8. The apparatus of claim 1 wherein said side walls partially overlay said edges of said traveling belts providing said sealing means.

9. The apparatus of claim 1 wherein said drive means drives said traveling belts in synchronous motion.

10. The apparatus of claim 1 including a coating of low zeta-potential material carried on said moving belts.

11. The apparatus of claim 10 wherein said material is methylcellulose.

12. Electrophoresis apparatus for separating cellular particles into at least one fraction band by means of inserting a sample stream of said particles into a buffer solution and impressing an electrical field in said buffer solution whereby the cells separate into said fraction band, said apparatus comprising:
   a water-tight enclosure housing containing said buffer solution;
   a separation chamber carried within said housing including a pair of spaced opposed moving walls and spaced opposed side walls defining said separation chamber;
   a pair of substrate assemblies having opposed substrate walls each of which carries an endless traveling belt defining said moving walls of said separation chamber;
   vacuum means communicating a source of vacuum to said substrate walls of said assemblies adhering said belts positively to said substrate front walls;
   means sealing marginal edges of said traveling belts preventing leakage of said buffer solution and sample stream past said edges and said side walls;

cooling means carried adjacent said front substrate wall cooling said separation chamber;

a coating of low zeta-potential material carried by each said moving belt; and drive means for moving said belt about said substrate assemblies in synchronization and in an endless fashion without slippage.

13. The apparatus of claim 12 wherein said vacuum means includes a plurality of suction ports formed in said front substrate walls against which belt is held by suction and a plurality of suction conduits interconnecting said suction ports in the form of grid means which support said front plate against deformation inwardly.

14. The apparatus of claim 12 including tensioning means maintaining said traveling belt tensioned and tightly held against the walls of said substrate assemblies and wherein each said front substrate wall includes a sloped portion exerting a force on said belt pulling same tightly against the wall for sealing.

15. The apparatus of claim 1 wherein said chamber is oriented horizontally.

* * * * *